United States Patent [19]

Hills

[11] Patent Number: 4,473,970

[45] Date of Patent: Oct. 2, 1984

[54] METHOD FOR GROWING A BIOMASS IN A CLOSED TUBULAR SYSTEM

[76] Inventor: Christopher B. Hills, 13151 Pine St., Boulder Creek, Calif. 95006

[21] Appl. No.: 400,294

[22] Filed: Jul. 21, 1982

[51] Int. Cl.³ .................................................. A01G 7/00
[52] U.S. Cl. ............................................. 47/1.4; 55/107
[58] Field of Search .................... 47/1.4, 58; 55/107, 55/110, 155

[56] References Cited

U.S. PATENT DOCUMENTS

| | | | |
|---|---|---|---|
| 2,732,663 | 1/1956 | Dewey | 47/1.4 |
| 2,807,912 | 10/1957 | Bjorksten | 47/58 |
| 3,403,471 | 10/1968 | Clement et al. | 47/1.4 |
| 3,468,057 | 9/1969 | Buisson | 47/1.4 |
| 3,650,068 | 3/1972 | Meyer et al. | 47/1.4 |
| 3,955,317 | 5/1976 | Gudin | 47/1.2 |
| 3,955,318 | 5/1976 | Hulls | 47/1.4 |
| 4,217,728 | 8/1980 | Shimamatsu et al. | 47/1.4 |
| 4,253,271 | 3/1981 | Raymond | 47/1.4 |

Primary Examiner—Robert A. Hafer
Assistant Examiner—D. D. DeMille
Attorney, Agent, or Firm—Limbach, Limbach & Sutton

[57] ABSTRACT

The present invention is an improved method of growing a biomass in an aquaculture medium comprising enclosing the aquaculture medium containing seed amounts of a biomass in an enclosure in which the medium containing the biomass fills one-half of the enclosure and a $CO_2$ and air gaseous layer is above the medium and fills the other one half, growing the biomass in the medium within the enclosure in a predetermined growing cycle enhancing growth of the biomass in the medium by exposing it to continuous agitation by agitation means heat, by heating means, and illumination by a light source capable of causing photosynthesis in the biomass, and whereby $CO_2$ consumed from the medium and gaseous layer during photosynthesis in the biomass is continuously replenished by a $CO_2$ enrichment means and oxygen produced to the medium and gaseous layer during photosynthesis is extracted by extraction means.

16 Claims, 7 Drawing Figures

METHOD FOR GROWING A BIOMASS IN A CLOSED TUBULAR SYSTEM

BACKGROUND OF THE INVENTION

It has been known to grow algal biomass cultures in open air and closed pond systems. Open air cultivation of an algal biomass has many problems, one of which is the possibility of contamination of the algal growth by constituents in the air that contact the growing culture. Representative open air systems for cultivation of algae are shown in U.S. Pat. No. 3,650,068; U.S. Pat. No. 3,468,057; U.S. Pat. No. 4,217,728.

In order to properly grow algal cultures in a closed system several conditions must be present. There must be constant agitation of the aquaculture medium (liquid suspension) containing the growing algae, heating for maintenance of a proper climate within the closed systems, exposure of the algae to photosynthesizing light, and an adequate means to replace carbon dioxide ($CO_2$) to the aquaculture medium due to losses during photosynthesis. The absence of these conditions could prove fatal to the growing cycle of the algae.

As stated, closed systems for growing algal cultures are known, however, unlike open systems, one of the main problems in these systems is the efficient replacement of the $CO_2$ to the aquaculture medium for consumption during photosynthesis in the algal biomass during growth. The closed system, unlike the open air system cannot absorb $CO_2$ from the open atmosphere. So, there must be an artificial means by which $CO_2$ can be resupplied to the medium and atmosphere within the closed system.

Prior art closed systems all have methods by which $CO_2$ is replenished by the system. Generally the $CO_2$ is replenished by bubbling it into and through the medium. The prior art closed systems that use a bubble method for replacing $CO_2$ are represented U.S. Pat. No. 3,955,317; and U.S. Pat. No. 4,253,271.

However, none of the prior art of systems have an effective way to resupply $CO_2$ to the medium alone and the medium and atmosphere together within the closed system.

SUMMARY OF THE INVENTION

Generally, the present invention accelerates the growth of the biomass in the aquaculture by providing a controlled environment using an alternative greenhouse effect to harness solar heat in growing the biomass in a moving aquaculture medium. The solar heat source also provides photosynthesizing light to the growing biomass (algae in this case) and there is constant replacement of carbon dioxide in the medium lost during photosyntehsis. The improvement of the present invention being a method of growing the biomass in collapsible tubes, which are transparent to photosynthesizing lights, and $CO_2$ enrichment of the medium and atmosphere within the tubes while there is a conjunctive action of oxygen removal from the closed system for use in $CO_2$ production.

According to the present invention, an algal biomass, such as spirulina and chlorella, are grown in an aquaculture medium having nutrients for growth and the medium is constantly enriched with $CO_2$ for enhancement of photosynthesis in the chloroplasts of the biomass during growth. The aquaculture containing the algal biomass is enclosed in flexible and collapsible tubing, preferably polyethylene. The tubing can be laid out in any of a plurality of shapes, e.g. spiral, or zig-zag patterns. The tubing may be cemented to a flat sheet of thick polyethylene and the tubing and flat sheet form a mat. The tube ends are connected to a pump and the pump and tube form a continuous loop.

Alternatively, the tubular system can also be extended for several miles on open lands or deserts, but the placement of the tubes must be on a flat or slightly inclined land with less than a 7% gradient.

The pump mentioned above is used first to pump the aquaculture with initial amounts of seed culture of the biomass into the collapsible tubing. Along with this, filtered air is pumped into the tubing by separate blowers which inflate it. This will result in the tubing being half filled with the aquaculture medium containing the biomass and the other half filled with air initially. As will be described, the air is for inflation only and sufficient amounts of $CO_2$ will be added to the air inside the tubing to create a $CO_2$ and air gaseous layer above the medium. The pump continuously agitates the culture medium by pumping it in a single direction within the closed loop. The $CO_2$ and air gaseous layer over the medium is continuously moved within the tube by the forced air blower or blowers connected to the tubing.

The tubing being transparent to photosynthesizing light will allow the light to be transmitted to the biomass for purposes of photosynthesis in the chloroplasts. When photosynthesis takes place, $CO_2$ in the medium and in the gaseous layer within the tubing is consumed and oxygen is produced. To insure that there is continued photosynthesis in the chloroplasts of the biomass, $CO_2$ consumed is replaced and the oxygen produced is extracted from the system by the method of the invention.

In the present invention, the $CO_2$ is replaced to the closed system in two ways. First, $CO_2$ is replenished to the medium alone, and secondly, $CO_2$ is replaced to the medium and $CO_2$ and air gaseous layer within the tube.

The biomass grown by the method results in a quantum yield of 10 to 30 grams per day of edible product per square meter of aquaculture used.

The object of the present invention is to provide a method of growing an algal biomass in an aquaculture medium within a closed tubular system having a carbon dioxide and air gaseous layer and the biomass is exposed to continuous agitation by an agitation means, heating by heating means and illumination by light source capable of causing photosynthesis in the biomass, and the method continuously replenishes consumed carbon dioxide to the system and removes oxygen from the system.

Another object of the invention is to provide a method for enriching carbon dioxide consumed from the aquaculture medium and $CO_2$ and air gaseous layer due to photosynthesis of the biomass and extracting oxygen produced by biomass during photosynthesis.

A still further object of the invention is to use treated sewage as the aquaculture medium for growing the algal biomass.

Another object of the invention is to use at least one pump for continuously agitating the biomass during the growing cycle of the biomass.

A still further object of the invention is to provide a atmosphere within the tubing which consists of approximately 10% to 14% carbon dioxide and 90% to 86% air maintainable throughout the growing cycle of the biomass.

Another object of the invention is to provide a method of growing an algal biomass which will produce 10 to 30 grams per day of edible product per square meter of aquaculture used.

DETAILED DESCRIPTION OF THE DRAWINGS

Figure 1:
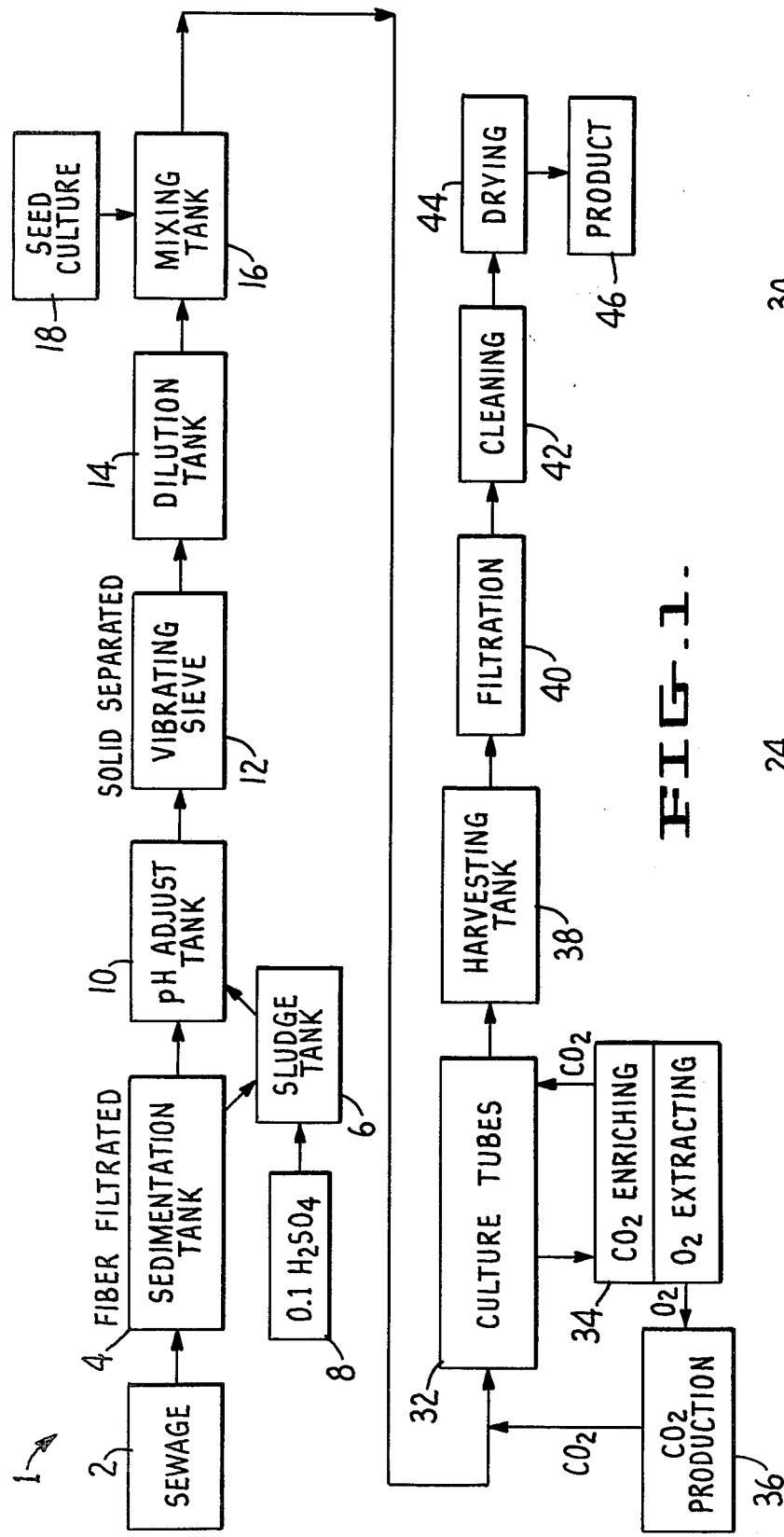
FIG. 1 shows a schematic block diagram of the method of the invention when treated sewage is the nutrient medium.

Referring to FIG. 1, a schematic block diagram of the method of the invention is shown generally at 1. When raw sewage is used to create aquaculture medium the final growth product is for animal consumption. The raw sewage at 2 is subject to fiber filtration in the sedimentation tank 4, and the resulting effluent is pumped to a pH adjustment tank 10. The sludge from the sedimentation tank 4 is deposited in sludge tank 6 where it is reacted on by a 0.1% sulfuric acid solution or $SO_2$ solution until a pH of 3 or 4 is reached. The solution is then pumped to pH adjustment tank 10 for pH adjustment of the solution to a level between 9.5 and 11.

After the pH level of the slurry containing effluent and solid particles has properly been adjusted, it is pumped to vibrating sieve 12 which separates the solid material from the liquid effluent. After separation of the solid particles from the liquid effluent is pumped to dilution tank 14. The effluent which enters dilution tank 14 is subsequently diluted, and the resulting liquid is one which provides an excellent aquaculture medium having sufficient nutrients for growing a biomass in it.

After proper dilution in dilution tank 14, the aquaculture medium is pumped to mixing tank 16 where it is combined with initial amounts of seed culture 18 of the biomass. After proper mixing of the aquaculture medium and seed culture, the aquaculture containing the seed culture is pumped to the culture tubes 32. However, prior to the aquaculture containing the seed culture entering the culture tubes, a gaseous mixture of 90% air and 10% carbon dioxide is bubbled into and through it.

Figure 1A:
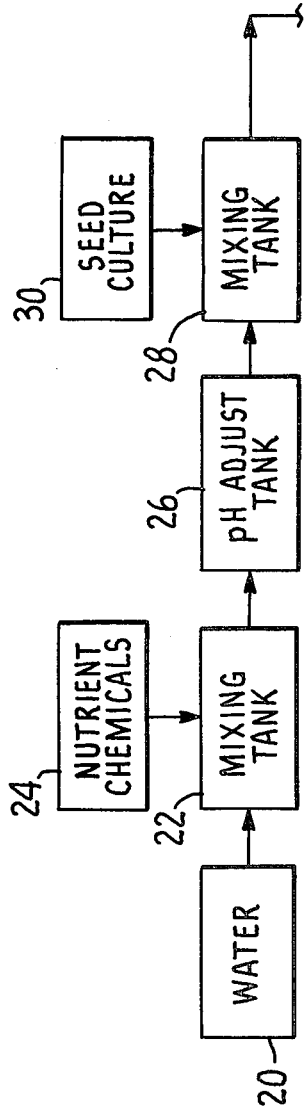
FIG. 1a shows a schematic block diagram of the method of the invention when water containing chemical nutrients is the nutrient medium.

Referring FIG. 1a, a schematic block diagram is shown for the production of a aquaculture if raw sewage is not used. This is the aquaculture medium used if the final product is for human consumption. Water 20 and nutrient chemicals 24 are mixed in mixing tank 22. After mixing, the solution is pumped to pH adjust tank 26, where the pH is adjusted to the proper level between 9.5 and 11. Once the pH has been adjusted, the solution is pumped to mixing tank 28, where it is mixed with seed culture 30. The aquaculture containing the seed culture is then pumped to the culture tubes 32, however, prior to reaching the tubes a gaseous mixture of approximately 10% to 14% $CO_2$ and 90% to 86% air is bubbled into it. From this point both methods are identical.

During the entire growing cycle of the biomass in tube 32, certain amounts of the aquaculture medium containing the growing biomass are extracted and passed through the carbon dioxide enriching and oxygen extracting apparatus 34. Within apparatus 34 carbon dioxide is enriched to the medium and oxygen extracted and fed to carbon dioxide production apparatus 36.

Once the biomass reaches the correct point in the growing cycle, it is pumped along the aquaculture medium to harvesting tank 38. After the biomass is harvested, it is filtered at 40, cleaned at 42, and dryed at 44. After drying there is a finished edible product 46 that can be used for human or animal consumption.

Figure 2:
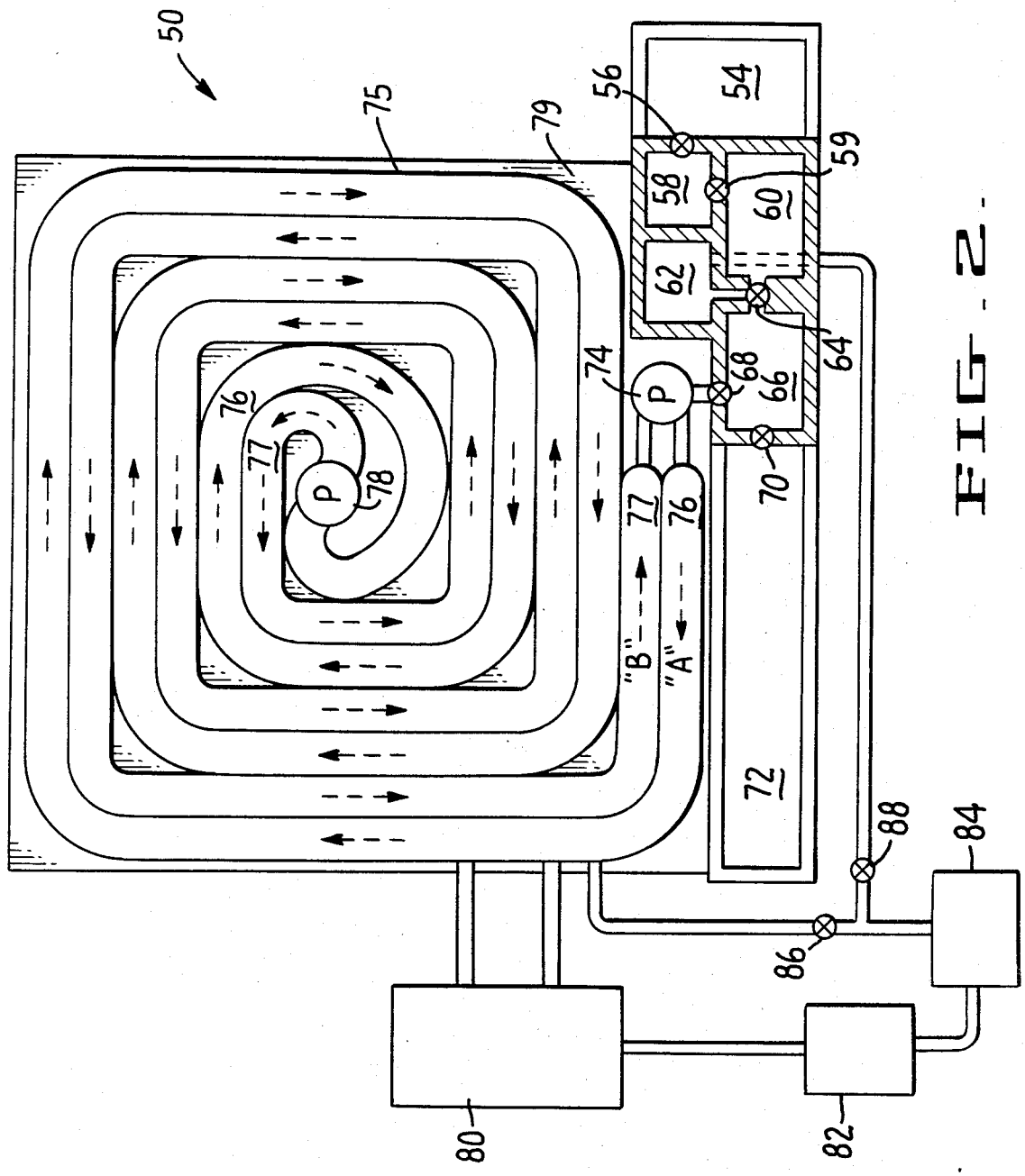
FIG. 2 shows the tubular system in a spiral pattern for practicing the method of the invention.

Referring to FIG. 2, a tubular system for growing the biomass, configured in a spiral pattern, is generally shown at 50. The system shown in FIG. 2 uses the effluent from treated sewage as an aquaculture medium; however, water treated with nutrient chemicals can be used. The effluent from sewage pond 54 passes to pH adjustment tank 58 when valve 56 is opened. The FIG. 2 system does not necessarily utilize a sedimentation tank, sludge tank, vibrating sieve or dilution tank as depicted in the FIG. 1 system. For example, these elements are not required in the event nutrient chemicals or certain types of sewage are used. Once effluent has achieved the proper pH level, it is pumped to mixing tank 60 through valve 59. In mixing tank 60 the seed biomass culture is added to the aquaculture medium.

After mixing, the aquaculture containing the seed biomass is pumped to side tank 66 through valve 64. Upon passing through valve 64 a gaseous mixture of 90% to 86% air and 10% to 14% $CO_2$ is bubbled to the aquaculture entering side tank 66.

The aquaculture medium containing the biomass in side tank 66 is pumped into the supply side 76 of a tube 75. The tube 75 is preferably constructed of transparent thin material which will collapse when not filled with the aquaculture and inflated with the air and $CO_2$ blown into it. The tube 75 is preferably constructed of a polyethylene material; however, various other types of materials which have similar properties to a thin polyethylene can be used. The seamless tube 75, although not having self-supporting structural strength, does 2have sufficient strength for enclosing the aquaculture medium containing the growing biomass and a charge of certain gases which inflate the tube to its maximum diametric shape.

The pump 74 takes a suction on side pond 66 until the proper amounts of aquaculture containing the biomass fill the bottom half of tube 75, which includes the supply side 76 and return side 77. Simultaneously with the filling of the tube 75 with the medium, blowers are used to inflate the remaining upper half of tube 75 with a gaseous layer. (The blowers are not shown). The blowers blow filtered air into medium in the tubes which combine with a bubbled mixture of $CO_2$ and air to produce a gaseous layer above the medium consisting of air and $CO_2$. The blowers continually circulate the $CO_2$ and air within the upper half of the inflated tube above the aquaculture.

Once tube 75 is filled with the aquaculture medium, valve 68 is closed and pumps 74 and 78 continually pump the aquaculture medium containing the biomass in direction "A" in supply section 76 and in direction "B" in return section 77. The continuous pumping agitates the aquaculture medium during the entire growing cycle.

During the growing cycle, the biomass is exposed to sunlight which causes photosynthesis in the chloroplasts of the biomass. Although the primary embodiment uses sunlight as the photosynthesizing light source, artificial light capable of causing photosynthesis in the biomass can be used. In the photosynthesis process, $CO_2$ is consumed and oxygen is given off by the biomass. In order to replace the $CO_2$ consumed from the medium and the gaseous layer above the medium, $CO_2$-enriching and oxygen-extracting apparatus 80 is connected to tube 75. The apparatus 80 will enrich the medium with $CO_2$ and return the $CO_2$ enriched medium to the tubing for further photosynthesis in the biomass. The oxygen extracted by the apparatus 80 is directed to diesel or gasoline engine 82 or a drying machine (not shown). The oxygen extracted is fed into the air inlet of the engine or drying machine or other device and the device will give off as a by-product $CO_2$ which is returned to the system. The $CO_2$ from the device enters mixing tank 84 which mixes filtered air with the $CO_2$ to produce a 90% to 86% air and 10% to 14% $CO_2$ gaseous mixture. The gaseous mixture in tank 84 is then directed through valve 86 to be bubbled directly into the tube 75 and/or through valve 88 to replenish tank 62.

In most cases, tube 75 is disposed on a flat sheet or flat layer 79 of black 10 ml thick plastic or polyethylene which is used as a solar collector for heating tube 75. The radiant heat energy of the sun is absorbed by the black surface 79 and helps maintain the proper climate within the tube 75 during the growing cycle. In other situations where the mat is floated on a pond, the flat layer is clear to allow light to pass through it to reach plant life below. However, a thermal heating layer is created below the mat which will retain heat for heat maintenance in the system.

Once the entire growing cycle has been completed, valve 68 and valve 70 are opened and the aquaculture containing the grown biomass is pumped through side tank 66 to store/harvest pond 72. After the aquaculture and grown biomass in store/harvest pond 72, it is harvested for final conversion into a food product. The method of harvesting will be subsequently described.

Figure 3:
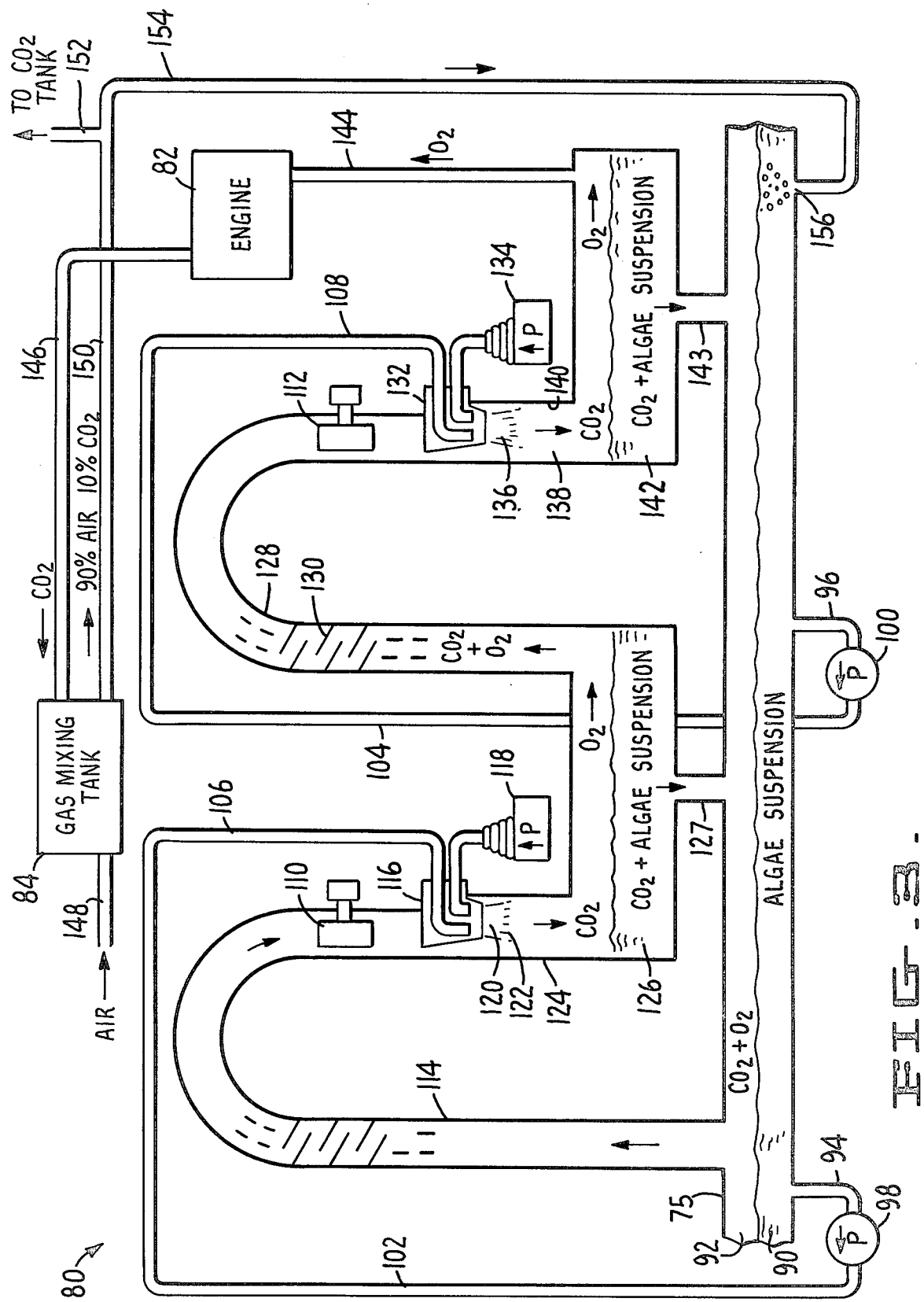
FIG. 3 shows the system for $CO_2$ enrichment to the medium and $CO_2$ production for bubbling into the tubular system.
Figure 4:
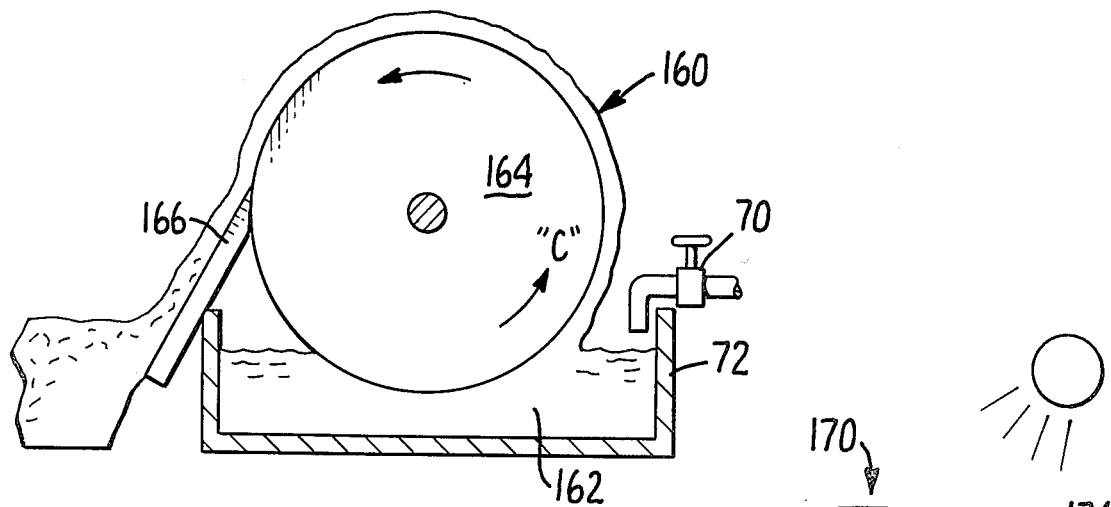
FIG. 4 shows the harvesting method for harvesting the biomass grown in the tubular system by the method of the invention.

Referring to FIG. 3, apparatus 80 for $CO_2$ enrichment of the aquaculture medium and oxygen removal from the system is shown and its method of operation will hereinafter be described.

The $CO_2$ enricher and oxygen removal apparatus is designed to remove and separate $CO_2$ and oxygen gases from the gaseous layer above the aquaculture medium. The apparatus will, by its method of operation, dissolve captured $CO_2$ in the aquaculture medium for use as a carbon source to carry out photosynthesis in the chloroplasts of the growing biomass. The oxygen separated in the apparatus is drawn off for other purposes. Although the described use of the apparatus of FIG. 3 is for separation of $CO_2$ and oxygen from the gaseous layer above the aquaculture medium, it can also be used to capture $CO_2$ from other sources. In such cases, the other sources could be gases output from other engines, dryers, boilers etc., not connected to the present apparatus. The only requirement is that the gas has some level of $CO_2$ contained therein.

The gases from these other sources will be mixed with the $CO_2$ input to tank 84.

Some of the gases from these sources require washing that is, scrubbing, prior to input into the apparatus. If such gases are used, a gas washing apparatus would be disposed adjacent to the source of the gas for carrying out that function.

When $CO_2$ gas produced by any source is desired to be used for input into the closed system of the invention, it must be soluble in water. In order for $CO_2$ to be soluble in water it must reach at a minimum a temperature of 31.1° C. The method of heating the $CO_2$ to ensure that the temperature of it is above 31.1° C. will be subsequently described.

Referring again to FIG. 3, pump 98 takes a suction on pipe 94 removing a portion of the biomass suspension 90 (aquaculture containing the growing biomass). Pump 98 pumps the portion of the biomass suspension 90 into pipe 102, where at point 106 a positive electric charge is placed on the biomass suspension. After the biomass suspenion has been positively charged, it enters insulated nozzle 116. Simultaneously, air pump 118 pumps air into nozzle 116. Within nozzle 116 the charged biomass suspension and air produce a positively charged spray 120 which is sprayed from the nozzle.

Fan 110 rotates such that it draws a portion of the $CO_2$ and air gaseous layer from within tube 75. The portion of the gaseous layer removed enters the pipe 114 and travels past fan 110 and down past nozzle 116.

Area 122 is the area below pipe 114 into which the charged spray 120 is directed. The area has a dielectric, preferably polyesther, disposed on the walls of the area creating an electrostatic chamber having a $CO_2$ and air atmosphere (flow from pipe 114). The positively charged spray in the electrostatic chamber causes the molecules of the $CO_2$ and oxygen to oppositely polarize. Because of the positive nature of the spray, the dielectric disposed along the walls, of area 122 will tend to align as a negative pole thus giving a negative charge to the walls. The $CO_2$ molecules polarize negatively while the oxygen molecules polarize positively. The oxygen molecules being positively polarized will tend to be attracted to the dielectric disposed on the walls while the $CO_2$ molecules being negatively polarized are attracted to the positively charged droplets of falling spray thus forming $CO_2$ and biomass suspension 126. The $CO_2$ and biomass suspension is a $CO_2$ enriched aquaculture which is gravity fed through pipe 127 back into tube 75.

The oxygen molecules and uncombined $CO_2$ molecules are removed from above the $CO_2$ enriched biomass suspension 126 by fan 112 and drawn into pipe 128. This is a second stage of $CO_2$ enriching of the biomass suspension. There can be any number of stages of $CO_2$ enrichment as desired.

For the second stage, pump 100 takes a suction on the biomass suspension 90 through pipe 96. Pump 100 pumps the suspension through pipe 104. The biomass suspension is positively charged in section 108 of pipe 104 and the positively charged biomass suspension is provided to nozzle 132 within which it is combined with air from air pump 134. The $CO_2$ and oxygen (air) are drawn into pipe 128 by fan 112 pass through baffles 130, disposed within pipe 128, and are deposited in electrostatic chamber 138 having a dielectric disposed on the walls. In electrostatic chamber 138, the positively charged biomass suspension oppositely polarizes the $CO_2$ and oxygen molecules. The $CO_2$ combines with the charged droplets of the biomass suspension to form $CO_2$ enriched biomass suspension 142 which is gravity fed back into tube 75 via pipe 143. The uncombined $CO_2$ and oxygen molecules are drawn off or pumped through pipe 144 to be burned in gasoline or diesel engine 82 which produces the $CO_2$ as a by-product. The $CO_2$ produced by engine 82 or the drying machine is pumped through pipe 146 to mixing tank 84 where it is combined with filtered air to form the gaseous solution containing 90% to 86% air and 10% to 14% $CO_2$. The outflow from mixing tank 84 in pipe 150 provides the gaseous solution of air and $CO_2$ to pipe 152, which connects to $CO_2$ tank 62 (FIG. 2) and pipe 154, which allows direct bubbling into the system.

As previously stated, in order for $CO_2$ gas to dissolve in water, it must have a temperature greater than 31.1° C. In most cases, the temperature of the $CO_2$ being exhausted from engine 82 or other device (not shown) is above 31.1° C. However, in the passage of the $CO_2$ from engine 82 to mixing tank 84, there can be dissipation of heat from the gas causing its temperature to drop below 31.1° C. Additionally. even if the gas does have a temperature above 31.1° C. when it reaches tank 84 it can fall below 31.1° C. if the temperature of the air it is mixed with is below 31.1° C. This is particularly true since 10% to 14% of $CO_2$ is mixed with 90% to 86% of air.

To overcome this problem, the air entering the mixing tank from pipe 148 has a temperature significantly above 31.1° C. The temperature is great enough such that even if the temperature of the $CO_2$ is significantly below 31.1° C., it will be raised above 31.1° C., so that it will dissolve in the medium as it is bubbled into the system at 156.

Referring to FIG. 4, the harvesting method is generally shown at 160. After the growing cycle of the biomass is completed, the grown biomass and aquaculture are pumped from tube 75 through side tank 66 and valve 70 into store/harvest pond 72. To harvest the biomass from the aquaculture, rotary filter 164 is used. The rotary filter rotates in direction "C" and has a vacuum suction drawing the biomass and aquaculture to the periphery. The apparatus is so constructed that it will allow liquid to pass through to the interior of the filter but hold the grown biomass on the periphery. The liquid which is sucked through the filter is expelled from it for separate disposal. The biomass which is held to the outer periphery of the rotary filter and will remain so attached until it experiences the edge of scraper 166 which scrapes the biomass from the periphery of the rotary filter.

The rotary filter intake pipe is moved throughout the store/harvest tank until substantially all the biomass has been recovered. After the biomass has been recovered, it is sent through the filtration, cleaning, and drying steps to produce the final edible product. By use of the method of this invention the quantum yield of the biomass is between 15 and 30 grams per square meter of aquaculture which is higher than previously known methods of cultivating biomass cultures.

An alternative method of harvesting contemplated by the invention uses a horizontal belt filter that automatically washes the harvested biomass and removes the washing liquid by vacuum in the same way as removal of liquid takes place using the raking filter.

Referring to FIG. 5, a cross-sectional view of a second embodiment of the invention is shown generally at 170. In the second embodiment, tube 174 is placed in a trough (on or above the ground) or trench 172 in the earth. If a trough is used it can be constructed of concrete, fiberglass or other heat retaining material. The tube is constructed of the same material as described in the first embodiment (preferred embodiment) described above. The aquaculture containing the growing biomass fills substantially one half of the tube while the other half is filled with a gaseous layer of air and $CO_2$, as previously described.

The sun provides light and heat using the greenhouse effect. The radiant solar energy provides the photosynthesizing light for the chloroplast in the biomass and also it heats the tube and the earth surrounding the trough or trench in which the tube lies. Although not shown in FIG. 5, the trough or trench can be filled with rocks, salt, or other heat retaining crystals below the tube to enhance its heat retaining properties. This action maintains some level of climatic control within the tube when the sun goes down and no longer provides direct solar heating to the tube.

Referring to FIG. 6, a third embodiment of the invention is shown at 180. In this embodiment, an alternative method of heating the aquaculture and growing biomass is shown. In this method there are two trenches dug into the earth. It is contemplated that two troughs made of a suitable material on or above the ground can be used. Trench 182 is for the plastic tube 174 and its supporting heating structures and trench 184 is for the heat collecting assembly.

The heat collecting assembly disposed in trench 184 has insulating box 192 disposed in trench and rocks 194 disposed in the box. The rocks are covered with a solar collector 196. When the sun is shining, the collector will cause rocks 194 to be heated. The heated rocks will retain that heat long after the sun goes down. The heat retained by the rocks will be used for maintaining the climate control within the plastic tube as will be described. The trench, which has tube 174 disposed therein, has an insulating layer 200 and rocks 202 below the tube. Disposed between the two trenches is a blower 188 having pipe 186 connected to the heat generating trench 184 and pipe 190 connected to the trench 182 with plastic tube 174. Other heat retaining substances or crystals can be substituted for rocks 194 and 202. The substitutes can be rock salt, sea solids left from salt-making, Glauber's salt, slurry of various liquids or solutions of salt or fresh water. Thereafter the process is the same as for rocks.

During normal daylight hours direct sunlight heats the aquaculture containing the growing biomass by the greenhouse effect and the solar collector 196 heats rocks 194. At night after the sun goes down, to maintain the controlled climate within the plastic tube 174, blower 188 is activated drawing air over hot rocks 194 which provides hot air to pipe 186. After passing through the blower the hot air passes through pipe 196 and impinges on and heats rocks 202. The heated rocks 202 will give off heat to the tube as they cool, thus maintaining the proper climate control within tube 174.

Figure 7:
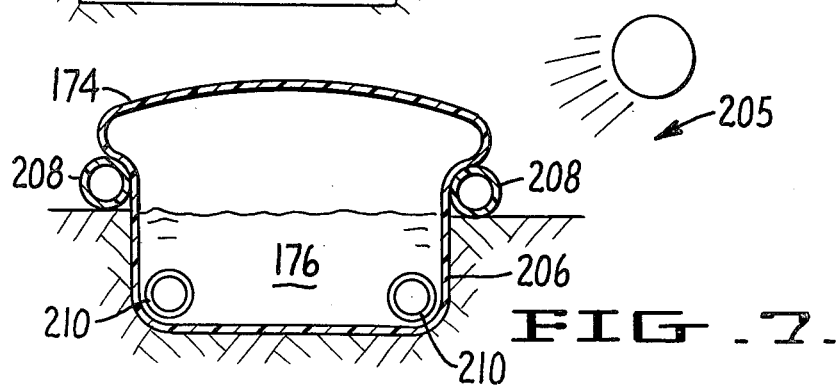
FIG. 7 shows a cross-sectional view of a fourth embodiment of the invention in which the tube containing the biomass culture is disposed in a trench and an alternative heating method is used for maintaining heat in the tubular system.

Referring to FIG. 7, the fourth embodiment of the method of the invention is shown. In this embodiment, the plastic tube 174 is disposed in trench 206 and an alternative heating method is used. Heating is provided by black polyvinyl chloride pipe 208 disposed on the outside of the tube and the pipe is heated by radiant solar energy. The hot air in the pipe 205 enters a blower (not shown) and is pumped through pipes 210 disposed within tube 174. Pipes 210 have small holes in them and hot air is forced through these holes and into the medium. This will provide heat to the aquaculture containing the growing biomass 176. During periods of night when the sun is not shining, the earth provides a certain amount of climate control within tube 174 along with the residual heat provided by the air flowing in the pipes 210.

Figure 5:
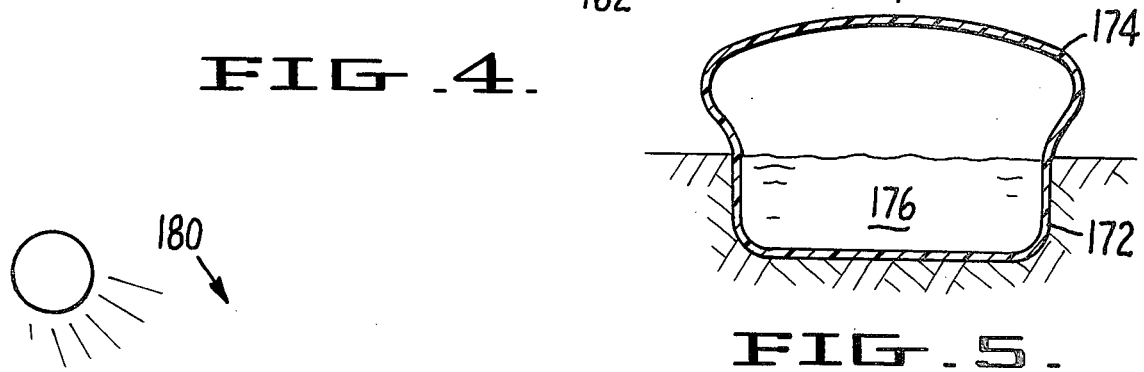
FIG. 5 shows a cross-sectional view of second embodiment of the invention in which the tube is disposed in a trench and an alternative heating method is used for heating the tubular system.
Figure 6:
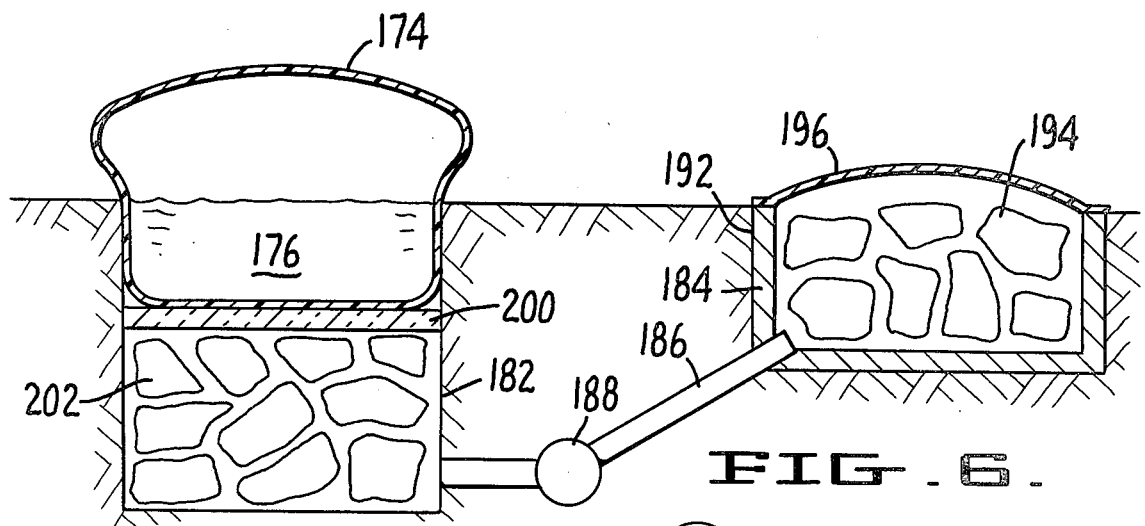
FIG. 6 shows a cross-sectional view of a third embodiment of the invention in which the tube containing the biomass culture is disposed in a trench and an alternative heating method is used for maintaining the heat in the tubular system.

The second, third and fourth embodiments of the invention in FIGS. 5, 6 and 7, respectively, also utilize the $CO_2$-enriching method previously described.

The inventor contemplates the invention to be all that is shown, described, and claimed to be an invention in the foregoing. However, there can be adaptations and changes to the present invention which are within the contemplation of the inventor. Thus, the inventor contemplates the invention to be all that is shown, described, and claimed to be the invention and all equivalents thereto.

I claim:

1. An improved method of growing a biomass in an aquaculture medium comprising the steps of:
   (1) seeding an aquaculture medium with a desired biomass;
   (2) placing the seeded medium in a sealed enclosure to partially fill the enclosure;
   (3) simultaneously bubbling carbon dioxide into the seeded medium while placing it into the enclosure;
   (4) filling the remainder of the enclosure with air and carbon dioxide to form a gaseous layer over the seeded medium;
   (5) continuously agitating the medium containing the biomass while in the enclosure;
   (6) providing a light source for the biomass for causing photosynthesis in the biomass;
   (7) removing a portion of the medium from the enclosure;
   (8) placing an electrical charge on the removed portion of the medium;
   (9) spraying the charged medium in an electrostatic chamber with a dielectric disposed on the walls and said chamber having carbon dioxide and oxygen atmosphere;
   (10) polarizing the carbon dioxide and oxygen molecules oppositely;
   (11) attracting and combining carbon dioxide molecules to spray droplets of the charged medium and forming carbon dioxide enriched medium;
   (12) replacing the carbon dioxide enriched medium to the enclosure;
   (13) repelling the oxygen molecules by the spray droplets of the charged medium;
   (14) extracting the oxygen molecules and uncombined carbon dioxide molecules from the chamber;
   (15) continuing steps 5 through 14, inclusive, until the growing cycle of the biomass is completed; and
   (16) removing the grown biomass from the enclosure for harvesting.

2. The improved method according to claim 1 wherein the carbon dioxide and oxygen atmosphere polarized in the electrostatic chamber is removed from the gaseous layer above the medium in the enclosure.

3. The improved method according to claim 1 wherein the extracted oxygen molecules and uncombined carbon dioxide molecules are directed to a carbon dioxide producing means and carbon dioxide produced in said means is bubbled into the enclosure.

4. The improved method according to claim 3 wherein the carbon dioxide is scrubbed prior to being bubbled into the enclosure.

5. The improved method according to claim 1 wherein heat is provided to the enclosure and medium by a heating means to enhance growth of the biomass.

6. The improved method according to claim 5 wherein the heating means includes an external heat source that heats the medium and enclosure by a conduction method.

7. The improved method according to claim 5 wherein the heating means includes radiant solar energy.

8. The improved method according to claim 1 wherein the enclosure is polyethylene tubing.

9. The improved method according to claim 8 wherein ends of the tubing engage the agitation means and the tubing and agitate means define a closed loop.

10. The improved method according to claim 9 wherein the agitation means includes at least one pump.

11. The improved method according to claim 8 wherein the tubing is arranged in a spiral pattern.

12. The improved method according to claim 8 wherein the tubing is arranged in a zig-zag pattern.

13. The improved method according to claim 1 wherein the gaseous layer above the medium in the enclosure is approximately 10% to 14% carbon dioxide and 90% to 86% air.

14. The improved method according to claim 1 wherein the light source is radiant solar energy.

15. The improved method according to claim 1 wherein the light source is artificial light capable of causing photosynthesis in the biomass.

16. The improved method according to claim 1 wherein the aquaculture medium has a pH level between 9.5 and 11.

* * * * *